United States Patent [19]

Buenemann et al.

[11] Patent Number: 4,990,695

[45] Date of Patent: Feb. 5, 1991

[54] PROCESS FOR PURIFYING CRUDE GLYCEROL

[75] Inventors: Thomas Buenemann, Zevenhuizen; Johannes C. Oudejans, Zevenaar, both of Netherlands; Pietro Gamba; Aldo Rampi, both of Cremona, Italy

[73] Assignee: Unilever Patent Holdings B.V., Rotterdam, Netherlands

[21] Appl. No.: 391,280

[22] Filed: Aug. 9, 1989

[30] Foreign Application Priority Data

Aug. 9, 1988 [EP] European Pat. Off. ........... 88201702

[51] Int. Cl.$^5$ ...................... C07C 29/76; C07C 31/22
[52] U.S. Cl. .................................................. 568/869
[58] Field of Search ......................................... 568/869

[56] References Cited

FOREIGN PATENT DOCUMENTS

| 142541 | 9/1948 | Australia | 568/869 |
|---|---|---|---|
| 0080684 | 8/1985 | European Pat. Off. | |
| 126827 | 7/1983 | Japan | 568/869 |
| 24100 | of 1904 | United Kingdom | 568/869 |

OTHER PUBLICATIONS

Soviet Inventions Illustrated, week 8643, No. 86-283915/43, Derwent Publications Ltd., Abstract.
Japan, vol. 7, No. 263 (C-196), Nov. 24, 1983; 58-144-333, Abstract.
Japan, vol. 8, No. 30 (C-209), Feb. 8, 1984; 58-192-840, Abstract.
Vogel, "Practical Organic Chemistry", 3rd ed. (1957), pp. 50, 51 and 130–134.
Aldrich, "Catalog Handbook of Fine Chemicals", (1986–1987), pp. 1659–1661.

Primary Examiner—J. E. Evans
Attorney, Agent, or Firm—Cushman, Darby & Cushman

[57] ABSTRACT

The invention provides a process for purifying crude glycerol such as splitters crude, soaplye crude and methanolysis crude which comprises a microfiltration step over a filter material on a ceramic support preferably comprising alumina. Preferably the filter material comprises zirconia and/or alumina. Preferably the process further comprises the step of distillation and/or treatment with ion exchange resins. Also the process may involve a combination of microfiltration and ultrafiltration.

10 Claims, No Drawings

PROCESS FOR PURIFYING CRUDE GLYCEROL

The invention relates to a process for purifying crude glycerol, which means here crude glycerol obtained from oils and fats by saponification, hydrolysis or methanolysis. More in particular the invention relates to the purification of so called splitters' crude that is crude glycerol obtained by the high-pressure steam splitting of oils and fats. Methanolysis crude obtained by reaction of triglyceride oils with methanol can also be used, but this material has to be diluted to an aqueous solution before it can be processed according to the present invention. Sometimes mixtures of splitters crude, methanolysis crude and/or soaplye crude are also processed according to the present invention with good results. Soaplye crude and splitters' crude contain a good deal of water, fatty acid, fatty acid glycerides, phosphatides, soaps, nitrogenous materials, colour bodies etc which need to be removed during purification. Soaplye crude also contains an important amount of sodium chloride. Methanolysis crude, however, may not contain water, but does contain the other impurities mentioned above.

For the purification of crude glycerol a number of techniques have been used comprising steps such as chemicals treatment, conventional filtration, ultrafiltration using organic polymer membranes treatment with ion exchange resins, electrodialysis, distillation etc. Often two or more of these methods are combined to obtain food grade or high quality glycerol. More specifically it is known from EP-A-141 358 (Henkel) to purify crude glycerol as to obtain food grade glycerol by a combination of alkali treatment and distillation. JP-A-58144333 (Nippon Oils and Fats) discloses the combination of alkali treatment followed by use of anion-exchange and cation exchange resins. SU-A-1 216 176 (Synth. Rubber Res.) discloses the separation of fatty acids from splitters crude by "ultrafiltration" followed by removal of water by evaporation yielding technical grade glycerol. According to this citation crude glycerol is pumped through a series of tubular membranes consisting of cellulose acetate, fluorplast or polysulfonamide with a pore size below 50 nm (i.e. 45 nm) at a pressure of 0.3–0.4 MPa and at a temperature of 48° C.

The above known methods are not quite satisfactory because to obtain high quality glycerol the costs of chemical treatment are high, also the cost of equipment is high and the losses of glycerol are appreciable. Moreover also sludge processing and effluent treatment have become more and more expensive recently. Also the process of SU-A-1 216 176 has the disadvantage of a low throughput (about $15 \text{l.h}^{-1} \text{l.m}^{-2}$) even at an increased pressure 0.3–0.4 MPa and at low glycerol concentration (9.6–14%).

The present invention provides a process for purifying glycerol, avoiding some of the above mentioned disadvantages, which process comprises a step involving microfiltration over a filter material on a ceramic support including a carbon support. Ceramic material has the advantage of high mechanical resistance, can be used in wide temperature and pH ranges, they are easy to clean and moreover have a high lifetime. Moreover certain filters as e.g. zirconia on a support of alumina have the additional advantage that no or hardly any intermediate cleaning of the filter is required. Preferably the ceramic support comprises alumina. The filter material comprises a ceramic material, preferably zirconia and/or alumina. Preferably the method also comprises a distillation step and/or a step involving treatment with ion exchange resins. Efficient treatment with ion exchange resins involves both contacting with a cation exchange resin as well as with an anion exchange resin. Contacting with alternating cation exchange and anion exchange resins, which can be either weak or strong in activity is recommendable. Preferably the purification process according to the invention comprises a combination of microfiltration and ultrafiltration.

Microfiltration is here understood to be filtration involving the use of a filter material having a pore size in the range of $1.10^{-6}$ to $1.10^{-8}$ m. In the case of ultrafiltration the pore size range is below $1.10^{-8}$ m. It is preferred that over the filter module a pressure drop in the order of magnitude of 0.05 to 0.4 MPa takes place.

Some advantages obtainable by the process according to the present invention are:

1. high quality glycerol is obtained.
2. chemicals consumption is reduced, and consequently less sludge is being formed.
3. the loss of glycerol is less.
4. the cleaning of this type of microfilters is more easily achieved than the cleaning of conventional (micro) filters.
5. higher filtration throughput.
6. simple equipment, therefore continuous, reliable processing.

Chemicals treatment involving precipitation with chemicals as often practiced according to the prior art requires conventional filtration (plate and frame filters) which are cumbersome to operate.

In a preferred embodiment of the invention the process also comprises an ultrafiltration step, which follows immediately after the microfiltration step. Ultrafiltration then serves to remove proteins and several other organic contaminants including polyglycerols. Surprisingly ultrafiltration also removes a substantial part of the amino acids (if present) and this is possibly due to some kind of agglomeration in the crude glycerol.

Suitable filter materials employed in the ultrafiltration unit (UF-module) are inorganic (e.g. zirconia) and especially polymeric organic materials such as those based on polysulfone and suitable other polymeric material on carrier.

The crude glycerol to be purified according to the present invention dependent on its origin may contain impurities like proteins, colour bodies, fatty acid esters, water and salt. Splitters' crude and soap lye crude as processed according to the present invention contain from 8–80, preferably from 20 to 55 (w.w.) of glycerol. Methanolysis crude is usually first diluted with water to similar concentrations. Splitters crude often first has to be concentrated or e.g. mixed with methanolysis crude and/or distilled soaplye crude before it is purified according to the present invention.

It is preferred to adjust the pH of the crude glycerol before subjecting it to a microfiltration step to a value between 9 and 12 preferably between 10 and 12. This pH adjustment can be effected by judicious addition of hydroxide (e.g. alkali hydroxide or alkaline earth hydroxide) material or mineral acid. The addition of a small amount of calcium hydroxide, optionally with some sodium hydroxide to obtain a pH of 11 is quite satisfactory for splitters crude. Also the crude glycerol so treated should preferably be kept at a temperature between 60° and 100° C. before being subjected to microfiltration and optionally ultrafiltration.

The invention is illustrated by the following examples:

EXAMPLE 1

Splitters' crude (10% glycerol) was subjected to microfiltration using a pilot plant MF module made of alumina which had a filter surface of 0.2 m$^2$, the pore size of the membrane was $2.10^{-7}$ m.

Splitters crude (200 l) with a glycerol content of 10% (w.w.) was heated to a temperature of 70° C. This temperature was maintained for 45 minutes and the material was circulated over the module at a flow rate of 4,000 l/h whilst the pressure drop across the MF membrane was kept at 0.1 MPa.

Within 2.0 hours 80 l splitters crude were filtered, thus the average flow rate through the membrane was 200 l.h$^{-1}$.m$^2$. The initial impurity levels for total fatty matter and organic impurities were reduced from 1.0% to 0.20% and 2.5% to 0.5% (w.w.) respectively. The aqueous, purified glycerol so obtained was then distilled to obtain a good technical grade glycerol. If an ion exchange step was included before distilling the quality was further improved to a pharmaceutical grade.

EXAMPLE 2

Splitters crude which had been concentrated to 50% glycerol content (w.w.) was subjected to microfiltration using the MF-module of Example 1 followed by ultrafiltration. 200 l of the splitters crude were heated to and kept at a temperature of 70° C. after mixing with 0.57 kg Ca(OH)$_2$. The pH was about 12. After maintaining the temperature for 0.5 hours the splitters crude was circulated over a ceramic MF module (as described in Example 1) at a flow rate of 4,000 l/h while the pressure drop across the MF membrane was kept constant at 0.2 MPa. Within 1 hours 84 l splitters crude were filtered, thus the average permeate flow rate through the membrane was 210 l.h$^{-1}$.m$^{-2}$ (calculated as 100% glycerol). The initial impurity level for total fatty matter and inorganic impurities (ash) was thus reduced from 2.3% to 0.40% and 3.8% to 1.0% respectively.

The filtrate so obtained was then subjected to ultrafiltration over a pilot plant UF module having a filter surface of 1.6 m$^2$, the pore size of the polysulfone membrane employed was $5.10^{-9}$ m. Microfiltrated splitters (200 l) crude with a glycerol content of 50% were heated and kept at a temperature of 70° C. and then circulated at a flow rate of approximately 4,000 l/h whilst the pressure drop across the UF module was kept constant at 0.1 MPa. Within 1 hour 40 l splitters crude were filtered, thus the average permeate flow rate through the membrane was 13 l.h$^{-1}$ l.m$^{-2}$ (calculated as to 100% glycerol). The removal of impurities was determined by colour absorption at 278 nm, i.e. prior to UF this was 10.5 and after UF 3.6. Subsequently the material was treated by ion exchange resins and concentrated to 99.7% (w.w.) by vacuum evaporation of water. The glycerol thus obtained was of pharmaceutical and food grade quality.

EXAMPLE 3

Splitters crude from which part of the water has been evaporated to obtain a 20% (w.w.) glycerol content was purified by microfiltration followed by ultrafiltration. The experiments were carried out by using a MF module with a filter surface of 0.2 m$^2$ and membrane pore size of $2.10^{-7}$ m. 200 l of splitters crude were heated and kept at a temperature of about 60° C. and mixed with some Ca(OH)$_2$ as to obtain a pH of 11.5.

After keeping the liquid at that temperature for a period of 45 minutes the splitters crude was circulated over the MF- module at a flow rate of about 4000 l/h with a pressure drop across the membrane of about 0.1 MPa.

Within 5 hours, 190 l of the splitters crude were filtered with a permeate flow rate through the membrane of 190 l.h$^{-1}$ l.m$^{-2}$. After microfiltration the filtered solution was perfectly transparent. The filtrate so obtained was then subjected to ultrafiltration over a pilot plant UF-module with a filter surface of 0.5 m$^2$ and pore size of $5.10^{-9}$ m. The microfiltrated splitters crude (110 l) with a glycerol content of 20% (w.w.) was circulated at a temperature of 40° C. maximum and at pressure of 2.8 MPa with a pressure drop across the UF module of about 0.1 MPa. Within 1.5 h, about 80 l of splitters crude were filtered with a permeate flow rate through the membrane of 106 l.h$^{-1}$.m$^{-2}$. The removal of the impurities was determined by colour absorption at 278 nm i.e. prior to UF it is 15.8 and after UF 6.95. This material was then treated with cation and anion exchange resins and concentrated to 99.3% pure glycerol of high quality, meeting US Pharmacopoeia 20 quality.

EXAMPLE 4

Splitters crude having a 30% (w.w.) glycerol content was first subjected to microfiltration on an industrial scale. The turbid splitters crude was heated to a temperature of 80° C. and mixed with Ca(OH)$_2$ in order to reach pH 11. After keeping at the temperature of 80° C. for about 1 h the splitters crude was fed to a microfiltration loop having a membrane with a pore size of $2.10^{-7}$ m and circulated over the series of modules at a flow rate of 80 m$^3$/h, whilst the pressure drop across each microfiltration module was about 0.2 MPa.

Within 3 h, 15 m$^3$ of splitters crude were filtered. Considering that the loop had a surface of about 11.4 m$^2$ a flow rate through the membrane was obtained of about 130 l.h$^{-1}$.m$^{-2}$ (calculated as 100% glycerol). The filtrate was a limpid, pale yellow liquid with an ash content of about 0.05%. Then the microfiltration loop was washed in countercurrent with an aqueous diluted mineral acid solution, which took 30–40 minutes in order to reach the original filtration performance again.

The filtrate obtained in the microfiltration step was then subjected to ultrafiltration on an industrial scale.

The filter unit had a filter surface of about 100 m$^2$ and the UF membranes had a pore size of $5.10^{-9}$ m.

The microfiltered solution after heating to 40° C. was fed at 2.5 MPa pressure to the UF unit and circulated at a flow rate of about 12 m$^{-3}$/h whilst the pressure drop across the UF membrane was initially 0.1 MPa. The filtrate flow rate was approximately 3 m$^3$/h. When the pressure drop across the membrane had increased to 0.2 MPa, the filtering surface was considered dirty and was cleaned. In 8 hours 20 m$^3$ of microfiltered solution were subjected to ultrafiltration.

The removal of organic colour bodies was determined by colour absorption at 278 nm i.e. prior to UF 6.0, after UF 4.0. After treatment with ion exchange resins the purified dilute glycerol was concentrated to 99.5% by vacuum evaporation of water. This glycerol so obtained was of pharmaceutical quality and had an excellent colour stability upon heating.

EXAMPLE 5

Splitters crude which had been concentrated to 50 (w.w.) glycerol content was subjected to microfiltration using a pilot plant MF membrane made of zirconia supported on alumina, with a filter surface area of 0.2 m$^2$ and a pore size of $5.10^{-8}$ m.

The splitters crude was heated to and kept at a temperature of 90°–95° C. after mixing with Ca(OH)$_2$. The pH was about 11.5. After maintaining the temperature for 0.5 hours the splitters crude was circulated over the ceramic MF membrane at a flow rate of 4,000 l/h while the pressure drop across the MF membrane was kept constant at 0.14 MPa. Within 1 hour 140–150 l splitters crude were filtered, thus the average permeate flow rate through the membrane was 350–380 l.h$^{-1}$.m$^{-2}$ (calculated as 100% glycerol).

The initial impurity level for total fatty matter and inorganic impurities was thus reduced from 0.24 to 0.04 and 0.55 to 0.20% respectively.

Subsequently the material was treated with ion exchange resins and concentrated to 99.7% (w.w.) by vacuum evaporation of water. The glycerol thus obtained was of pharmaceutical and food grade quality.

COMPARATIVE EXPERIMENT

In this example splitters crude containing 50% (w.w.) glycerol had been pretreated in a conventional pretreatment. In the first step glycerol was treated with sulphuric acid to bring the pH at 2 to 2.5. This was done at a temperature of 90° C. during 15 minutes. Then lime (as a 40 wt % Ca(OH)$_2$ slurry) was added to bring the pH up to 11.5. The system was kept at 90° C. for 0.5 hour. Then the solids were filtered off over a conventional filter. The initial impurity levels for total fatty matter and inorganic impurity were reduced from 0.26% and to 0.06% and from 1.0% to 0.42%.

The splitters crude after filtration was subjected to a series of ion exchange resins for further purification, in the same way as in example 5. After the ion exchange and an additional bleaching step with active carbon the splitters crude was concentrated up to 99.7 % glycerol. In contrast with the product of example 5 the glycerol now obtained was not of pharmaceutical and/or food grade quality. Moreover the amount of glycerol obtained from the ion exchange resins before complete deactivation of the resins was about 50 % less than the amount of glycerol obtained from the resins after treatment of the splitters crude by microfiltration. This illustrates the higher degree of purification which is obtained by the microfiltration process of Example 5.

EXAMPLE 6

In a 66 hours continuous trial crude glycerol, concentrated up to 50% glycerol, was subjected to microfiltration using a pilot plant MF membrane made of zirconia supported on alumina with a filtration area of 0.2 m$^2$ and a pore size of $5.10^{-8}$ m.

The concentrated splitters crude, having a pH of 4.5, was continuously fed to a filter feed tank to which also—continuously—lime was added (as a 40 wt % Ca(OH)$_2$ slurry) to bring and maintain the pH at 11.5. The temperature in the feed tank as well as during microfiltration was kept between 90° and 95° C. During the microfiltration the lime treated splitters crude was circulated over the MF membrane at a flow rate of 4,000 l/h while the pressure drop across the membrane was kept at 0.12 MPa.

The filtration was continued for 66 hours during which the average filtration flow was 310 l.h$^{-1}$.m$^{-2}$ (calculated as 100 % glycerol). During this filtration period no fouling of the membrane was observed and consequently no membrane cleaning was required. The permeate glycerol was then subjected to a series of ion exchange beds in which further purification took place. After bleaching and end evaporation a 99.7% pharmaceutical and food grade glycerol was obtained.

We claim:

1. A process for purifying crude glycerol in aqueous solution, comprising the steps of obtaining the crude glycerol from oils and fats by saponification, hydrolysis or methanolysis, and microfiltrating over a filter material having a pore size in the range of from $1 \times 10^{-6}$ to $1 \times 10^{-8}$ m on a ceramic support.

2. A process according to claim 1, wherein the ceramic support material comprises alumina.

3. A process according to claim 1, wherein the filter material comprises ceramic material.

4. A process for purifying crude glycerol in aqueous solution, comprising the steps of obtaining the crude glycerol from oils and fats by saponification, hydrolysis or methanolysis, and microfiltrating and ultrafiltrating in combination over a filter material having a pore size less than $1 \times 10^{-8}$ m on a ceramic support.

5. A process according to claim 1, wherein the process further comprises the step of treatment with ion exchange resins and/or distillation.

6. A process according to claim 4, wherein the ultrafiltration step is conducted over a filter material which comprises an organic polymeric material.

7. A process according to claim 1, wherein the crude glycerol starting material is an aqueous solution and contains 8 to 80% (w.w.) of glycerol and has been obtained by saponifying, hydrolysis or methanolysis of oils or fats.

8. A process according to claim 7, wherein the crude glycerol starting material is an aqueous solution containing 20 to 55% of glycerol.

9. A process according to claim 1, wherein prior to any filtration the pH of the crude glycerol starting material is adjusted to a value between 9 and 12 at a temperature between 60°–100° C.

10. A process according to claim 1 characterized in that the microfiltration is conducted over a filter material having a pore diameter between $5.10^{-8}$ m and $20.10^{-8}$ m.

* * * * *